United States Patent [19]

Lange et al.

[11] Patent Number: 4,588,487
[45] Date of Patent: May 13, 1986

[54] PROCESS FOR THE PREPARATION OF 3'-HALODIPHENYLETHERS

[75] Inventors: Barry C. Lange, Levittown; Edward M. Szapacs, Center Valley, both of Pa.

[73] Assignee: Rohm and Haas Company, Philadelphia, Pa.

[21] Appl. No.: 776,350

[22] Filed: Sep. 16, 1985

[51] Int. Cl.$^4$ .................. C07C 41/18; C07C 43/263; B01J 19/12

[52] U.S. Cl. .............. 204/157.82; 568/585; 204/157.92

[58] Field of Search ............ 568/585; 204/163 R, 204/158 HA

[56] References Cited

U.S. PATENT DOCUMENTS

| | | | |
|---|---|---|---|
| 3,950,435 | 4/1976 | Takahashi et al. | 71/124 |
| 3,966,453 | 6/1976 | Takahashi et al. | 71/105 |
| 4,046,798 | 9/1977 | Bayer et al. | 71/88 |
| 4,093,446 | 6/1978 | Bayer et al. | 71/109 |
| 4,358,308 | 11/1982 | Swithenbank | 71/98 |
| 4,419,122 | 12/1983 | Swithenbank | 71/98 |
| 4,485,254 | 11/1984 | Tanger | 560/21 |

FOREIGN PATENT DOCUMENTS 1079303 6/1980 Canada .

OTHER PUBLICATIONS

Silbert, Jour. Amer. Oil Chemist Soc. (1969) 615–619.
Wilson, "The Reaction of Halogens with Silver Salts of Carboxylic Acids", *Organic Reactions*, vol. IX, Chapter 5, pp. 333–387.
Sosnovsky, "Reactions of Halogens with Salts of Carboxylic Acids", *Free Radical Reactions in Preparative Organic Chemistry*, pp. 383–386.
Larock, "Organomercurials as Reagents and Intermediates in Organic Synthesis", *New Applications of Organometallic Reagents in Organic Synthesis*, pp. 257, 264, 265, (1976).
Bamford and Tipper, "Halogenolysis (Halogenodemetallation) of Organometallic Compounds", *Chemical Kinetics*, vol. 12, pp. 135–176 (1973).
Makarova, "Reaction of Organomercury Compounds, Part 2", *Organometallic Reactions*, pp. 411–421 (1971).
Meyers and Fleming, 44, *J. Org. Chem.*, 3405 (1979).
Kochi, "Metal Complexes in Organic Oxidations", *Organometallic Mechanisms and Catalysis*, pp. 99–103 (1978).
Silbert, 46, *J. Am. Oil Chemists Soc.*, 615 (1969).
Buchler and Pearson, "Survey of Organic Synthesis", pp. 352–353 (1970).
Buchler and Pearson, "Survey of Organic Synthesis", vol. 2, pp. 354–355 (1977).

*Primary Examiner*—Bernard Helfin
*Attorney, Agent, or Firm*—John C. Demeter

[57] ABSTRACT

This process relates to the halodecarboxylation of 3'-carboxydiphenylether salts using diacyl peroxides, molecular bromine, moderate temperature, an inert atmosphere and atmospheric pressure to afford 2-chloro-4-trifluoromethyl-3'-bromo-4'-nitrodiphenylether.

10 Claims, No Drawings

PROCESS FOR THE PREPARATION OF 3'-HALODIPHENYLETHERS

BACKGROUND OF THE INVENTION

This invention relates to a process for the preparation of 2-chloro-4-trifluoromethyl-3'-bromo-4'-nitrodiphenylether.

The preparation of certain diphenylethers is generally reported in the literature to be accomplished by reacting a suitably substituted phenol or alkali metal salt thereof with a suitably substituted halobenzene in the presence of an alkaline agent in a polar aprotic solvent and optionally including a catalyst. See, for example, U.S. Pat. Nos. 3,966,453; 3,950,435; 4,046,798; 4,093,446; 4,358,308 and Canadian Pat. No. 1,079,303.

Diphenylethers prepared by the above techniques are also generally reported in the literature to be used as precursors in preparing certain other diphenylether derivatives. For example, the 4'-halo or 4'-nitro derivatives are prepared by halogenating or nitrating an otherwise suitably substituted diphenylether. Further, 3'-hydroxydiphenylethers can be converted to alpha-oxymethylene carboxylic esters by condensation with alpha-halo esters in the presence of bases such as potassium carbonate or hydroxide. These alpha-oxymethylene carboxylic esters can then be converted to the corresponding carboxylic acids, acid chlorides or amides. Still further, 3'-alkoxydiphenylethers can be made by reacting the corresponding 3'-halodiphenylether prepared by the above described techniques with a carbinol in an inert nonpolar solvent in the presence of base.

SUMMARY OF THE INVENTION

This invention relates to an improved process for the preparation of 2-chloro-4-trifluoromethyl-3'-bromo-4'-nitrodiphenylether which comprises halodecarboxylation of a diphenylether having the formula

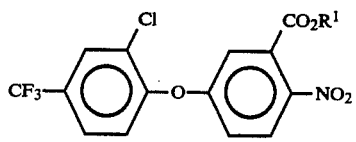

where $R^1$ is an alkali metal or alkaline earth metal salt in a polar aprotic solvent in a substantially inert atmosphere at temperatures from about 65° C. to about 150° C. at about atmospheric pressure, optionally in the presence of light, in the presence of a diacyl peroxide having the formula

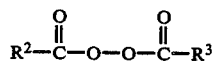

where $R^2$ and $R^3$ are, independently aliphatic, aromatic or alkylaromatic and in the presence of molecular bromine.

DETAILED DESCRIPTION OF THE INVENTION

This invention relates to a process utilizing about atmospheric pressure, a substantially inert atmosphere, moderate temperatures, molecular bromine, and a suitable diacyl peroxide. Unless otherwise stated, "equivalents" should be understood as meaning on a molar basis. In particular, this invention relates to the preparation of 2-chloro-4-trifluoromethyl-3'-bromo-4'-nitrodiphenylether which comprises halodecarboxylation of a diphenylether having the formula

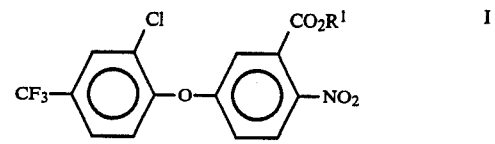

where $R^1$ is an alkali metal or alkaline earth metal salt in a polar aprotic solvent in a substantially inert atmosphere, at temperatures from about 65° C. to about 150° C. at about atmospheric pressure, optionally in the presence of light, in the presence of a diacyl peroxide having the formula

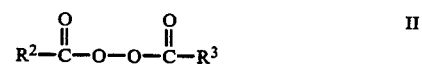

where $R^2$ and $R^3$ are, independently aliphatic, aromatic or alkylaromatic and in the presence of molecular bromine.

In the above process, typical polar aprotic solvents that can be utilized include ethers such as diethyl ether, tetrahydrofuran (THF), glyme and the like; acetonitrile; dimethylformamide (DMF) and the like. Acetonitrile is the preferred solvent.

Generally, from about one to about five equivalents of diacyl peroxide of Formula II is utilized for each equivalent of substrate (Formula I). Preferably, about three equivalents of diacyl peroxide is utilized per equivalent of substrate (Formula I).

The amount of molecular bromine ($Br_2$) utilized generally is from about one to about 5 equivalents for each equivalent of substrate (Formula I). Preferably, about two equivalents of molecular bromine ($Br_2$) are utilized per equivalent of substrate (Formula I).

The presence of a source of light may optionally be utilized in the process of the present invention. When employed, the light should have a power rating of at least about 25 watts, and preferably at least about 75 watts.

Temperatures utilized for the process of the present invention are from about 65° C. to about 150° C., preferably from about 75° C. to about 110° C.

The process of the present invention should be carried out in a substantially inert atmosphere such as nitrogen or argon.

The alkali metal or alkaline earth metal salts of Formula I can be prepared by standard techniques known in the art such as those described above or by the process disclosed in U.S. Pat. No. 4,485,254 which is incorporated herein by reference. For example, the alkali metal salts such as sodium, potassium, lithium and the like, and the alkaline earth metal salts such as magnesium, calcium and the like, are prepared by treating the carboxylic acid with an alkali metal hydroxide or hydride, or an alkaline earth metal hydroxide or hydride, such as sodium hydroxide, potassium hydroxide, calcium hydroxide, sodium hydride, magnesium hydride and the like in an inert or substantially inert solvent.

Examples of the diacyl peroxides of Formula II suitable for use in the process of the present invention include diacetyl peroxide, dibenzoyl peroxide, di-n-octanoyl peroxide, di-heptafluoro-n-propionyl peroxide, acetyl benzoyl peroxide, di-p-chlorobenzoyl peroxide, phthaloyl peroxide and the like. The diaromatic diacyl peroxides are preferred and dibenzoyl peroxide is most preferred.

The 2-chloro-4-trifluoromethyl-3'-bromo-4'-nitrodiphenylether prepared by the process of this invention can be used as a herbicide or as an intermediate in the preparation of other herbicidal diphenylethers by techniques known to those skilled in the art.

The following examples are presented to further illustrate the process of this invention and are not intended to limit the breadth and scope of the invention in any way.

EXAMPLE 1

Preparation of 2-chloro-4-trifluoromethyl-3'-bromo-4'-nitrodiphenylether With Irradiation A 100 ml, three-necked round-bottomed flask was fitted with a thermometer, condenser, nitrogen inlet adapter and stir bar. The apparatus was flushed with nitrogen while drying with a heat gun. Potassium 2-chloro-4-trifluoromethyl-3'-carboxy-4'-nitrodiphenylether (0.20 g) was added to the flask and dissolved in acetonitrile (20 ml). Bromine (0.12 g, 1.5 equivalents) dissolved in acetonitrile (10 ml) was added to the flask and the mixture heated to reflux (80° C.). When reflux was achieved benzoyl peroxide (0.12 g, 1 equivalent) was added in one portion and reflux continued for 4 hours under nitrogen with constant irradiation. The equipment had been wrapped in aluminum foil with a portion of the foil opened to allow a 100-watt light bulb to shine into the reaction mixture.

Thin-layer chromatographic analysis on silica gel using 25/75 v/v EtOAc/hexane solvent indicated the presence of the 3'-bromo compound by comparison with a known standard.

EXAMPLE 2

Preparation of 2-chloro-4-trifluoromethyl-3'-bromo-4'-nitrodiphenylether Without Irradiation The potassium salt of 2-chloro-4-trifluoromethyl-3'-carboxy-4'-nitrodiphenylether (2.0 g), benzoyl peroxide (1.2 g, 1 equivalent) and bromine (1.2 g, 1.5 equivalents) were refluxed in acetonitrile for 15 hours under nitrogen. Additional quantities of benzoyl peroxide (total 2.0 extra equivalents) were added periodically during the reflux period when thin-layer chromatographic analysis indicated that the benzoyl peroxide was gone. An additional quantity of bromine (0.5 equivalent) was also added during this period. After the reflux period, the reaction was cooled to room temperature and the solvent was removed under vacuum. The residue was dissolved in methylene chloride, and the resulting solution was washed with aqueous sodium bisulfite, aqueous sodium bicarbonate, dried over anhydrous magnesium sulfate and concentrated under vacuum to a brown oil (2.7 g). Thin-layer chromatographic analysis of this product indicated the presence of 2-chloro-4-trifluoromethyl-3'-bromo-4'-nitrodiphenylether by comparison with a known standard using silica gel and 20/80 v/v EtOAc/hexane eluent.

The aqueous layer was acidified and extracted with methylene chloride. Concentration under vacuum of the methylene chloride extract provided an off-white solid (1.3 g). High-pressure liquid chromatographic analysis of this solid indicated that the solid contained about 50% 2-chloro-4-trifluoromethyl-3'-carboxy-4'-nitrodiphenylether (in the acid form, by comparison of its retention time with that of a known standard).

EXAMPLE 3

Preparation of 2-chloro-4-trifluoromethyl-3'-bromo-4'-nitrodiphenylether Without Irradiation A 500 ml, three-necked round-bottomed flask was fitted with a thermometer, condenser, nitrogen inlet adapter and stir bar. The apparatus was flushed with nitrogen while drying with a heat gun. The potassium salt of 2-chloro-4-trifluoromethyl-3'-carboxy-4'-nitrodiphenylether (10.0 g) was added to acetonitrile (150 ml). Bromine (6.0 g, 1.5 equivalents) in acetonitrile (50 ml) was added and the solution was heated to 60° C. (heating mantle). At this time, a portion of benzoyl peroxide (3.0 g, 0.5 equivalents) was added and the reaction mixture was heated to reflux at 80° C. Additional benzoyl peroxide (total 18.0 g, 3.0 equivalents) was added in 3.0 g portions every few hours. After refluxing for 15 hours, the mixture was cooled to room temperature and the acetonitrile was removed under vacuum. The residue was taken up in methylene chloride and the resulting solution washed with sodium bisulfite solution (aqueous 5% w/w), sodium hydroxide solution (aqueous 1 M), dried over magnesium sulfate and concentrated under vacuum to give a brown-yellow oil (7.8 g). A portion of this product (6.0 g) was purified by chromatography on a 14" long, 2" diameter silica gel (70-230 mesh) column using 10/90 v/v EtOAc/hexane. From the resulting fraction was isolated the pure 3'-bromo compound (2.5 g, corresponds to 34% yield based on 2-chloro-4-trifluoromethyl-3'-bromo-4'-nitrodiphenylether potassium salt, m.p. 56°–59° C.). NMR and infrared spectroscopic data are consistent with the proposed structure of the 3'-bromo compound. The combustion analysis of this product corresponded to 2-chloro-3'-bromo-4'-nitro-4-trifluoromethyldiphenylether, $C_{13}H_6BrClF_3NO_3$.

| Element | Calculated (%) | Found (%) |
|---------|----------------|-----------|
| C       | 39.38          | 39.55     |
| H       | 1.52           | 1.56      |
| Br      | 20.15          | 20.66     |
| Cl      | 8.95           | 8.73      |
| F       | 14.37          | 14.26     |
| N       | 3.53           | 3.47      |
| (O)     | 12.10          | (11.77)   |
|         | 100.00         | (100.00)  |

What is claimed is:

1. A process for preparing 2-chloro-4-trifluoromethyl-3'-bromo-4'-nitrodiphenylether which comprises reacting a diphenylether having the formula:

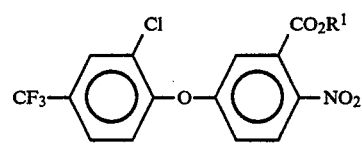

where $R^1$ is an alkali metal or alkaline earth metal salt with a diacyl peroxide having the formula:

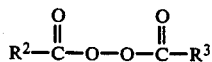

where $R^2$ and $R^3$ are, independently aliphatic, aromatic or alkylaromatic; and molecular bromine in a polar aprotic solvent, at about atmospheric pressure, in a substantially inert atmosphere at temperatures from about 65° C. to about 150° C. and optionally in the presence of light.

2. The process of claim 1 wherein from about one to about five equivalents of diacyl peroxide having the formula:

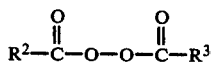

where $R^2$ and $R^3$ are, independently, aliphatic, aromatic or alkylaromatic; is utilized for each equivalent of diphenylether having the formula:

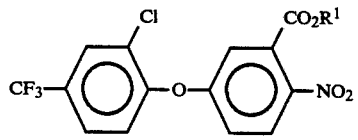

where $R^1$ is an alkali metal or alkaline earth metal salt.

3. The process of claim 2 wherein about three equivalents of said diacyl peroxide is utilized per equivalent of said diphenylether.

4. The process of claim 2 wherein the diacyl peroxide utilized is a diaromatic diacyl peroxide.

5. The process of claim 4 wherein said diacyl peroxide is dibenzoyl peroxide..

6. The process of claim 1 wherein from about one to about five equivalents of molecular bromine are utilized per equivalent of diphenyl ether having the formula:

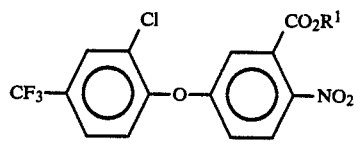

where $R^1$ is an alkali metal or alkaline eath metal salt.

7. The process of claim 6 wherein about two equivalents of molecular bromine are utilized per equivalent of said diphenylether.

8. The process of claim 1 wherein the reaction is carried out at temperatures between about 75° C. and about 110° C.

9. The process of claim 1 wherein at least about 25-watts of light are employed.

10. The process of claim 9 wherein at least about 75-watts of light are employed.

* * * * *